United States Patent [19]

Sweeny et al.

[11] Patent Number: 4,493,869

[45] Date of Patent: Jan. 15, 1985

[54] FRAGRANCE-RELEASING MICROCAPSULES ON A SEE-THROUGH SUBSTRATE

[75] Inventors: Norman P. Sweeny, North Oaks, Minn.; Keith E. Relyea, St. Joseph, Wis.; Wayne L. Brustad, St. Paul, Minn.

[73] Assignee: Minnesota Mining and Manufacturing Company, St. Paul, Minn.

[21] Appl. No.: 540,502

[22] Filed: Oct. 11, 1983

[51] Int. Cl.$^3$ ................................................. B32B 5/16
[52] U.S. Cl. .................................... 428/201; 428/323; 428/327; 428/343; 428/346; 428/354; 428/402.21; 428/905
[58] Field of Search ........... 428/402.2, 402.21, 402.22, 428/323, 201, 327, 405, 313.5, 346, 354, 343; 252/522 R, 522 A, 315.1; 424/37; 427/258, 261

[56] References Cited

U.S. PATENT DOCUMENTS

| | | | |
|---|---|---|---|
| 2,925,174 | 2/1960 | Stow | 428/346 |
| 3,016,308 | 1/1962 | Macaulay | 117/36.7 |
| 3,121,021 | 2/1960 | Copeland | 117/122 |
| 3,503,783 | 3/1965 | Evans | 117/47 |
| 3,516,846 | 6/1970 | Matson | 117/36.2 |
| 3,516,941 | 6/1966 | Matson | 252/316 |
| 3,778,383 | 12/1973 | Schibler et al. | 252/316 |
| 4,058,434 | 11/1977 | Vincent | 162/165 |
| 4,087,376 | 5/1978 | Foris et al. | 252/316 |
| 4,089,802 | 5/1978 | Foris et al. | 252/316 |
| 4,100,103 | 7/1978 | Foris et al. | 252/316 |
| 4,182,788 | 1/1980 | Vassiliades et al. | 428/313.5 |
| 4,201,404 | 5/1980 | Charbonneau et al. | 282/27.5 |
| 4,251,386 | 2/1981 | Saeki et al. | 252/316 |

FOREIGN PATENT DOCUMENTS

| | | | |
|---|---|---|---|
| 1156725 | 7/1966 | United Kingdom . | |
| 1329309 | 9/1973 | United Kingdom | 428/905 |
| 2006709 | 9/1978 | United Kingdom . | |
| 2041319 | 11/1979 | United Kingdom . | |
| 2062570 | 9/1980 | United Kingdom . | |
| 2048206 | 12/1980 | United Kingdom . | |

*Primary Examiner*—Paul J. Thibodeau
*Attorney, Agent, or Firm*—Donald M. Sell; James A. Smith; Carole Truesdale

[57] ABSTRACT

Fragrance releasing appliques are provided which comprise a transparent or translucent substrate bearing microcapsules in a binder on one surface and an adhesive on the remaining surface.

10 Claims, No Drawings

FRAGRANCE-RELEASING MICROCAPSULES ON A SEE-THROUGH SUBSTRATE

FIELD OF THE INVENTION

This invention relates to microencapsulated materials, articles containing microencapsulated materials and the method of preparing such articles. In particular, the present invention relates to microencapsulated materials bonded onto a transparent or translucent surface of a substrate with an adhesive on the back-side of the substrate. The microcapsules are on a printed surface and the transparent or translucent qualities of the substrate enhance the visual effect of the printed image.

BACKGROUND OF THE INVENTION

Encapsulated materials have been used for many years in a wide variety of commercial applications. Early uses of encapsulated materials included paper coated with capsules bearing coloring material therein which could be used as a recording medium. U.S. Pat. No. 3,016,308 discloses one of the early efforts using encapsulated material as the image source on recording paper. U.S. Pat. Nos. 4,058,434 and 4,201,404 show other methods of application of encapsulated coloring materials on paper substrates to be used as imaging media and the like. U.S. Pat. No. 3,503,783 shows microcapsules having coloring material therein which are ruptureable by the application of heat, pressure and/or radiation because of a metal coating on the surface of the capsule. These ruptureable microcapsules, in one embodiment, may be secured between a substrate and a photoconductive top coat to enable photosensitive imaging of the system.

A wide variety of processes exist by which microcapsules can be manufactured. These varied processes provide different techniques for producing capsules of varying sizes, alternative materials for the composition of the capsule shell and various different functional materials within the shell. Some of these various processes are shown in U.S. Pat. Nos. 3,516,846; 3,516,941; 3,778,383; 4,087,376; 4,089,802; 4,100,103 and 4,251,386 and British Patent Specification Nos. 1,156,725; 2,041,319 and 2,048,206. A wide variety of different materials may also be used in making the capsule shells, including gelatin and synthetic polymeric materials. A popular material for shell formation is the polymerization reaction product between urea and formaldehyde or melamine formaldehyde, or the polycondensation products of monomeric or low molecular weight polymers of dimethylolurea or methylolated urea with aldehydes. A variety of capsule forming materials are disclosed, for example, in U.S. Pat. Nos. 3,516,846 and 4,087,376 and U.K. Patent Specification Nos. 2,006,709 and 2,062,570.

As shown in these references, the principal utility of microencapsulated materials is in the formation of an opaque surface coated with the microcapsules in a binder. The microcapsules are ruptured by various means to release the material contained therein. In addition to release of physically observable materials such as ink in order to form a visible image, other types of active ingredients such as odor releasing materials, bacteriostatic materials, chemically active materials and the like have been provided in this manner.

SUMMARY OF THE INVENTION

The present invention relates to a new article containing ruptureable microcapsules. The novel article comprises a flexible substrate which is transparent or translucent and which has on one surface a coating comprising a binder resin having microcapsules dispersed therein and on the other surface a pressure sensitive or water-moistenable adhesive. The use of the transparent or translucent backing along with a printed image under the binder coating provides new visual characteristics and utilities to the microcapsule-coated articles. The images blend more naturally with the surface to which they are adhered and the articles may be used in novel manners such as art overlays.

DETAILED DESCRIPTION OF THE INVENTION

The present invention relates to an article comprising a flexible transparent or translucent substrate having at least one surface, a polymeric binder layer having microcapsules dispersed therein over said one surface, and a pressure sensitive or water-moistenable adhesive on the other surface of said substrate. The substrate is a film or sheet material which may effectively be of any polymeric film as long as the substrates are transparent or translucent. By "translucent" according to the present invention, it is meant that at least 50% (and preferably at least 75%) of incident visible light is transmitted or that at least 80% of light within a 50 nm band is transmitted through the substrate when adhered to a surface. The capsules in the present invention may comprise any ruptureable capsule containing an odorous ingredient therein. The size of the capsules should generally be in a range of an average diameter between 8 and 30 microns when the capsule payload is between 55 and 80% by weight of load to capsule. It is preferred that the capsules have an average diameter between 10 and 26 microns and it is most preferred that the capsules have a diameter between 12 and 25 microns.

The coating weight of binder and microcapsules should be at a coating weight of approximately one pound for 300 to 3000 square feet. Preferably the coating weight should be between approximately one pound for each 250 to 650 square feet. The capsules should form between 20 and 75 percent by volume of the total adhesive composition, and preferably between 50 and 65 percent of the total composition.

The nature and composition of the binder is not critical to the practice of the invention as long as the binder does not opacify the article or visually block the printed image.

The adhesive may be pressure sensitive or solvent sensitive (preferably water-activatable). It is generally preferred that the adhesive be pressure sensitive for ease of application. Well known acrylic and polyurethane pressure sensitive compositions are particularly desirable. Where the article is applied to the skin as a tattoo, the pressure sensitive adhesive must be hypoallergenic. Materials such as the pressure-sensitive, hypoallergenic, synthetic, acrylic adhesives used on surgical tapes such as that shown in U.S. Pat. No. 3,121,021 are particularly preferred.

The binder (with microcapsules) may be applied in either a continuous or discontinuous pattern over the image. The binder pattern usually corresponds to the pattern of the image but it may be random or generally applied over the entire printed surface.

Any class of polymeric binder including but not limited to polyurethanes, polyacrylates, polyvinyl resins, epoxy resins, polyamides, polyesters, polyolefins, starches, gum arabic, gelatin and the like may be readily used in the practice of the present invention.

The capsules may contain a wide variety of fragrant materials therein. The most preferred types of ingredients would be organic oils which are fragrance releasing materials which readily volatilize upon rupturing of the capsule. These may or may not also be colored.

The substrate, as previously noted may be any transparent or translucent polymeric film or web. Film materials such as polyesters, polyvinyl resins, cellulose acetate, cellulose accetate butyrate, cellulose acetate proprionate, polyolefins, and the like may be used. The so-called frosted tapes may be used and provide excellent substrates for the practice of the present invention. These tapes appear somewhat cloudy, but become more light transmissive upon application of the adhesive layer to a substrate.

The printed image may be partially precut so that the edge of the applique is the perimeter of the image, or any shape may be cut (e.g. circular, square, irregular) so that the transparency or translucency of the backing without printing thereon allows the image to stand out.

EXAMPLE

An oil having the aroma of Concord grapes was encapsulated in a urea-formaldehyde resin made according to the process of Example 20 of U.S. Pat. No. 3,516,941. The capsules had an average diameter of about 17 micrometers and an estimated payload of 64% by weight (ratio of weight of oil to total capsule weight).

A coating formulation was prepared comprising 54 parts capsules, 39 parts polyvinyl alcohol and 7 part Foamkill ® 836A (antifoam agent) in a water slurry. This formulation was coated at 3.5 lbs. per 1300 sq. ft. (dry weight) onto a glossy transparent cellulose acetate film label stock. The coating was made over the entire surface which had preprinted images of a personified grape thereon. The back-side of the film stock had been precoated with a hypoallergenic, acrylic pressure-sensitive adhesive with a release layer (strippable carrier layer) over the adhesive. Some samples were cut along the perimeter of the image and other samples were cut in circles circumscribing the image. The strippable layer was removed from the appliques and the samples applied to various surfaces including skin, paper, and the printed metal of a lunch pail. The transparency of the backing allowed the printed image to stand out clearly. On the skin, a good tattoo-like image was displayed that could be readily pealed off and provided contact to the skin with only hypoallergenic materials. On the lunch pail, the applique image appeared to be a novel addition to the existing image on the pail because of the relative invisibility of the backing material.

Die cuts of unprinted areas can also be made and applied to objects having printed or painted art work applied to give unique personalized microfragrance objects.

We claim:

1. A fragrance releasing article comprising:
   (A) a transparent or translucent organic polymeric carrier layer,
   (B) on one side of said carrier layer a pressure-sensitive or water-moistenable adhesive layer, and
   (C) on the other side of said carrier layer a printed image applied to said carrier layer, and
   (D) a non-opacifying fragrance releasing layer comprising microcapsules carrying a volatile, fragrant liquid therein and an organic binder resin adhering the microcapsules to the printed carrier layer.

2. The article of claim 1 wherein said carrier layer is transparent.

3. The article of claim 1 wherein said carrier layer is translucent.

4. The article of claim 1 wherein said carrier layer is a frosted organic polymeric layer which becomes more light transmissive when the adhesive layer is applied to a substrate.

5. The article of claim 1 wherein said microcapsules comprise gelatin.

6. The article of claim 1 wherein said microcapsules comprise capsules of urea-formaldehyde resin having average diameters between 8 and 30 micrometers.

7. The article of claim 1 wherein said microcapsules have an average diameter between 8 and 30 micrometers.

8. The article of claim 5 wherein said microcapsules have an average diameter between 8 and 30 micrometers.

9. The article of claim 1 wherein said pressure-sensitive adhesive is a hypoallergenic, synthetic, acrylic adhesive.

10. The article of claim 5 wherein said pressure-sensitive adhesive is a hypoallergenic, synthetic, acrylic adhesive.

* * * * *